United States Patent
Misle et al.

(10) Patent No.: US 10,485,625 B1
(45) Date of Patent: Nov. 26, 2019

(54) STERILE STAND FOR SUPPORTING SURGICAL INSTRUMENTS

(71) Applicants: Gayle Misle, Millbrae, CA (US); Trent J. Perry, Kaysville, UT (US)

(72) Inventors: Gayle Misle, Millbrae, CA (US); Trent J. Perry, Kaysville, UT (US)

( * ) Notice: Subject to any disclaimer, the term of this patent is extended or adjusted under 35 U.S.C. 154(b) by 0 days.

(21) Appl. No.: 16/161,411

(22) Filed: Oct. 16, 2018

Related U.S. Application Data

(63) Continuation-in-part of application No. 15/898,857, filed on Feb. 19, 2018.

(51) Int. Cl.
   *A61B 50/30* (2016.01)
   *A47F 7/00* (2006.01)

(52) U.S. Cl.
   CPC ........ *A61B 50/3001* (2016.02); *A47F 7/0028* (2013.01); *A61B 50/30* (2016.02)

(58) Field of Classification Search
   CPC ... A61B 50/3001; A61B 50/30; A47F 7/0021; A47F 7/0028
   USPC ...... 211/85.13, 69.1, 69.5, 70; 206/214, 1.7, 206/366, 365
   See application file for complete search history.

(56) References Cited

U.S. PATENT DOCUMENTS

| | | | | |
|---|---|---|---|---|
| 283,389 A | * | 8/1883 | Goodwin | B43K 13/00 15/423 |
| 648,928 A | * | 5/1900 | Davis | A61L 2/00 206/207 |
| 760,578 A | * | 5/1904 | Steinmetz | A47F 7/0028 211/60.1 |
| 769,592 A | * | 9/1904 | De Long | B43M 99/003 144/286.1 |
| 1,296,158 A | * | 3/1919 | Bonham | A45C 11/16 206/214 |
| 1,641,829 A | * | 9/1927 | Sheaffer | B43M 99/006 211/69.5 |
| 1,991,200 A | * | 2/1935 | Feinberg | B43M 99/001 211/69.5 |
| 2,354,118 A | * | 7/1944 | Hansen | B43K 23/04 211/69.5 |
| 2,511,537 A | * | 6/1950 | Migdow | B44D 3/02 206/1.7 |
| 2,523,877 A | * | 9/1950 | Pestolesi | A61M 5/008 206/366 |
| 2,557,420 A | * | 6/1951 | Elliott | A61L 2/26 206/210 |
| 2,666,967 A | * | 1/1954 | Poitras | A61B 5/150022 206/366 |
| 2,741,048 A | * | 4/1956 | Shelton | B44D 3/02 206/1.7 |

(Continued)

FOREIGN PATENT DOCUMENTS

| | | |
|---|---|---|
| EP | 0053206 A1 | 6/1982 |
| EP | 3042626 A1 | 7/2016 |

(Continued)

*Primary Examiner* — Michael Safavi
(74) *Attorney, Agent, or Firm* — Dennis L. Thomte; Thomte Patent Law Office LLC

(57) ABSTRACT

A sterile stand for supporting surgical instruments or medical tools such as needles, cannulas, syringes and injection needle assemblies. The stand includes a solid housing having upper and lower ends. The housing has a plurality of openings and bores formed therein which are configured to receive surgical instruments or medical tools therein.

1 Claim, 5 Drawing Sheets

(56) References Cited

U.S. PATENT DOCUMENTS

| | | | |
|---|---|---|---|
| 2,919,692 A | 1/1960 | Ackermann | |
| 3,273,701 A * | 9/1966 | Friedman | B65D 85/20 206/214 |
| 3,463,323 A * | 8/1969 | Riepe | B43M 99/007 211/69.5 |
| 3,593,856 A * | 7/1971 | Zander | A45C 11/34 211/69.5 |
| 3,866,992 A * | 2/1975 | Katz | B43M 99/007 211/69.5 |
| 4,121,719 A * | 10/1978 | Wilhelm | B43M 99/001 211/69.5 |
| 4,136,773 A * | 1/1979 | Booth | A45C 11/34 206/214 |
| 4,155,446 A * | 5/1979 | Aronson | G09B 19/0023 206/214 |
| 4,190,166 A * | 2/1980 | Allsop | A47F 7/0028 211/162 |
| 4,341,300 A * | 7/1982 | Roy | B43M 99/002 206/523 |
| 4,826,338 A * | 5/1989 | Kilpatrick | B43K 8/003 211/69.1 |
| 4,850,484 A * | 7/1989 | Denman | A61M 5/008 206/366 |
| 4,944,730 A * | 7/1990 | Plucinski | A61M 5/008 206/366 |
| 4,973,315 A * | 11/1990 | Sincock | A61M 5/3213 206/365 |
| 5,033,629 A * | 7/1991 | Caine | A47F 7/00 211/69.5 |
| 5,099,992 A * | 3/1992 | Heimreid | A61J 1/2096 206/366 |
| 5,163,549 A * | 11/1992 | Hayduchok | A45C 11/34 206/214 |
| 5,230,428 A * | 7/1993 | McShane | A61M 5/3213 206/363 |
| 5,232,103 A * | 8/1993 | Koenig | B43K 23/002 211/60.1 |
| 5,285,896 A * | 2/1994 | Salatka | A61M 5/3205 206/366 |
| 5,291,997 A * | 3/1994 | He | A61M 5/002 206/366 |
| 5,330,899 A | 7/1994 | DeVaughn | |
| 5,352,205 A | 10/1994 | Dales et al. | |
| 5,372,252 A | 12/1994 | Alexander | |
| 5,396,989 A * | 3/1995 | Hein | A61B 17/205 206/366 |
| 15,435,979 | 7/1995 | Miller et al. | |
| 5,447,243 A * | 9/1995 | Graber | B43M 99/008 206/371 |
| 5,462,163 A | 10/1995 | Berry | |
| 5,505,711 A | 4/1996 | Arakawa et al. | |
| 5,509,540 A * | 4/1996 | Pomerantz | A47F 7/0028 211/13.1 |
| 5,533,618 A | 7/1996 | Pickels, Jr. | |
| 5,544,764 A * | 8/1996 | Cima | B43M 99/008 211/60.1 |
| 5,676,856 A | 10/1997 | Brimhall | |
| 5,755,321 A * | 5/1998 | Wang | B43M 99/008 206/214 |
| 5,817,060 A | 10/1998 | Overton et al. | |
| 5,823,363 A * | 10/1998 | Cassel | A61M 5/008 211/60.1 |
| 5,833,057 A * | 11/1998 | Char | B01L 9/06 206/204 |
| 5,850,917 A * | 12/1998 | Denton | A61M 5/008 206/366 |
| 6,123,193 A * | 9/2000 | Vojtasek | A61M 5/3213 206/366 |
| 6,202,862 B1 * | 3/2001 | Acquaviva | B43K 21/003 211/60.1 |
| 6,346,094 B2 * | 2/2002 | West | A61M 5/002 206/365 |
| 6,401,931 B1 * | 6/2002 | Javell | A47F 7/0028 206/214 |
| 6,561,363 B1 * | 5/2003 | Willhite | A47F 7/0028 206/443 |
| 7,314,142 B2 * | 1/2008 | Lyman, Jr. | B43K 23/002 206/214 |
| 8,911,233 B2 * | 12/2014 | Moore | A61C 3/04 211/70.6 |
| 2002/0014560 A1 | 2/2002 | Diamond | |
| 2006/0106348 A1 | 5/2006 | Lichtenberg | |
| 2007/0134142 A1 | 6/2007 | Riley | |
| 2008/0085143 A1 * | 4/2008 | LaBrasca | A45C 11/34 401/131 |
| 2008/0164182 A1 * | 7/2008 | Pender | A45D 34/00 206/581 |
| 2008/0221516 A1 * | 9/2008 | Partika | A61B 50/20 604/110 |
| 2008/0243092 A1 | 10/2008 | Nilsson et al. | |
| 2009/0054866 A1 | 2/2009 | Teisen-Simony et al. | |
| 2009/0259201 A1 | 10/2009 | Hwang et al. | |
| 2011/0031136 A1 * | 2/2011 | Strain | B44D 3/04 206/1.7 |
| 2012/0085720 A1 | 4/2012 | Bettenhausen et al. | |
| 2012/0273446 A1 * | 11/2012 | Moore | A61C 3/04 211/85.13 |
| 2013/0328467 A1 * | 12/2013 | Carlton | A47F 7/0028 312/280 |
| 2014/0021079 A1 * | 1/2014 | Koller | A47F 7/0028 206/370 |
| 2014/0197120 A1 | 7/2014 | Seiwell | |
| 2014/0202903 A1 | 7/2014 | Dassonville et al. | |
| 2015/0239278 A1 * | 8/2015 | White | B43K 23/001 211/69.5 |
| 2016/0286922 A1 * | 10/2016 | Chorney | B43K 23/00 |
| 2016/0318661 A1 * | 11/2016 | Simakis | A45F 5/021 |
| 2017/0035522 A1 | 2/2017 | Roland | |

FOREIGN PATENT DOCUMENTS

| | | | | |
|---|---|---|---|---|
| GB | 2083005 | * | 3/1982 | A47F 7/0028 |
| JP | 03158170 A1 | | 7/1991 | |
| WO | 9740869 A1 | | 11/1997 | |
| WO | 2014109011 A1 | | 7/2014 | |
| WO | 2014115256 A1 | | 7/2014 | |

* cited by examiner

STERILE STAND FOR SUPPORTING SURGICAL INSTRUMENTS

CROSS REFERENCE TO RELATED APPLICATION

This is a Continuation-in-Part Application of application Ser. No. 15/898,857 filed Feb. 19, 2018, entitled STERILE STAND FOR SUPPORTING SURGICAL INSTRUMENTS.

BACKGROUND OF THE INVENTION

Field of the Invention

This invention relates to a sterile stand for supporting surgical instruments or medical tools such as epidural needles, blunt-tip cannulas, syringes and injection needle assemblies.

Description of the Related Art

Applicants have previously filed U.S. patent application Ser. No. 15/133,660 filed Apr. 20, 2016 entitled CANNULA AND NEEDLE ASSEMBLY and U.S. patent application Ser. No. 15/354,249 filed Nov. 17, 2016 entitled EPIDURAL NEEDLE ASSEMBLY. In U.S. patent application Ser. No. 15/354,249, during the use of components thereof, there are occasions when the epidural needle or cannula needs to be removed from the patient to add additional local anesthetic or fillers to a syringe connected to the epidural needle or cannula. It is important during this procedure to maintain the epidural needle or cannula in a sterile condition if it is to be used again. Prior to the invention of the co-pending application, maintaining the needle in a sterile condition required a two-handed technique. In the prior art procedure, one hand holds the syringe with the other hand removes the needle cap from the syringe. Then, the person must put the syringe down with one hand while the other hand grasps the needle cap and places it on the needle to keep it sterile. The invention of the co-pending application represents an improvement in the art. The instant invention represents a further improvement in the art.

SUMMARY OF THE INVENTION

This Summary is provided to introduce a selection of concepts in a simplified form that are further described below in the Detailed Description. This Summary is not intended to identify key aspects or essential aspects of the claimed subject matter. Moreover, this Summary is not intended for use as an aid in determining the scope of the claimed subject matter.

A sterile stand for supporting surgical instruments in a vertically disposed sterile manner is disclosed. The stand includes a solid housing having a horizontally disposed lower end, a horizontally disposed upper end, and upstanding sides extending between the lower and upper ends of the housing. First, second, third, fourth, fifth and sixth openings are formed in the upper end of the housing. An elongated and vertically disposed first cylindrical bore is formed in the housing and which has upper and lower ends. The upper end of the first cylindrical bore is in communication with the first opening and extends downwardly therefrom towards the bottom of the housing whereby the lower end of the first cylindrical bore is closed. An elongated and vertically disposed second cylindrical bore is formed in the housing which has upper and lower ends. The upper end of the second cylindrical bore is in communication with the second opening and extends downwardly therefrom towards the bottom of the housing whereby the lower end of the second cylindrical bore is closed. The first opening in the upper end of the housing and the first cylindrical bore are configured to have a first syringe selectively positioned therein. The second opening in the upper end of the housing and the second cylindrical bore are configured to have a second syringe selectively positioned therein.

The housing also includes an elongated and vertically disposed third cylindrical bore having upper and lower ends. The upper end of the third cylindrical bore is in communication with the third opening and extends downwardly therefrom towards the bottom of the housing whereby the lower end of the third cylindrical bore is closed. The third opening and the third cylindrical bore are configured to have a blunt-tip cannula or epidural needle positioned therein. The housing also includes an elongated and vertically disposed fourth cylindrical bore having upper and lower ends. The upper end of the fourth cylindrical bore is in communication with the fourth opening and extends downwardly therefrom towards the bottom of the housing whereby the lower end of the fourth cylindrical bore is closed. The fourth opening and the fourth cylindrical bore are configured to have a blunt-tip cannula or epidural needle positioned therein. The housing also includes an elongated fifth cylindrical bore having upper and lower ends. The upper end of the fifth cylindrical bore is in communication with the fifth opening and extends downwardly therefrom towards the bottom of the housing whereby the lower end of the fifth cylindrical bore is closed. A horizontally disposed first slot is formed in the upper end of the housing which has an upper end and a lower end with the first slot extending laterally from the fifth opening in the upper end of the housing. The fifth opening and the first slot are configured to have an injection needle assembly selectively positioned therein. The housing also includes an elongated sixth cylindrical bore having upper and lower ends. The upper end of the sixth cylindrical bore is in communication with the sixth opening and extends downwardly towards the bottom of the housing whereby the lower end of the side to sixth bore is closed. A horizontally disposed second slot is formed in the upper end of the housing which has an upper end and a lower end with the second slot extending laterally from the sixth opening. The sixth opening and the second slot are configured to have an injection needle assembly selectively positioned therein.

In one embodiment of the invention, the stand is square-shaped. In another embodiment of the invention, the stand is cylindrical-shaped. In yet another embodiment of the invention, the side walls of the stand are curved.

It is therefore a principal object of the invention to provide an improved sterile stand for supporting surgical instruments or medical tools therein.

A further object of the invention is to provide a sterile stand for supporting epidural needles, cannulas, and syringes therein and for supporting an injection needle assembly therein.

These and other objects will be apparent to those skilled in the art.

BRIEF DESCRIPTION OF THE DRAWINGS

Non-limiting and non-exhaustive embodiments of the present invention are described with reference to the following figures, wherein like reference numerals refer to like parts throughout the various views unless otherwise specified.

DESCRIPTION OF THE PREFERRED EMBODIMENT

Figure 1:
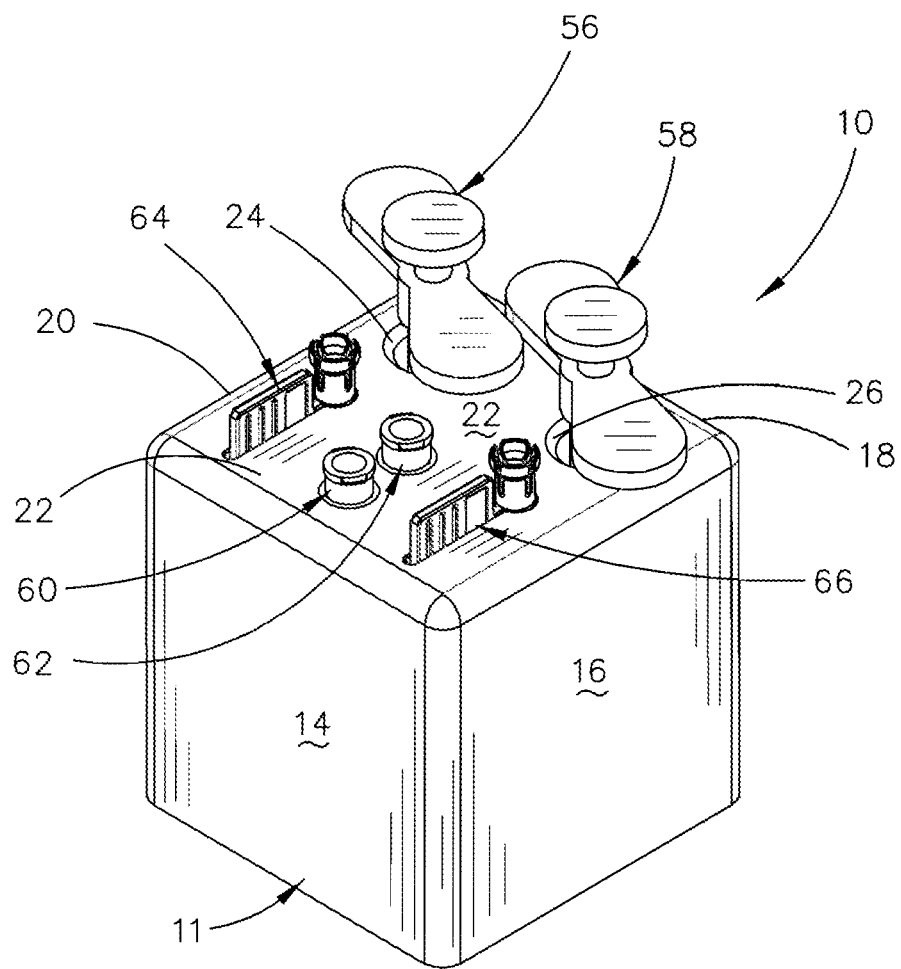
FIG. 1 is a perspective view of one embodiment of the stand of this invention and which illustrates various surgical instruments or medical tools positioned therein.
Figure 2:
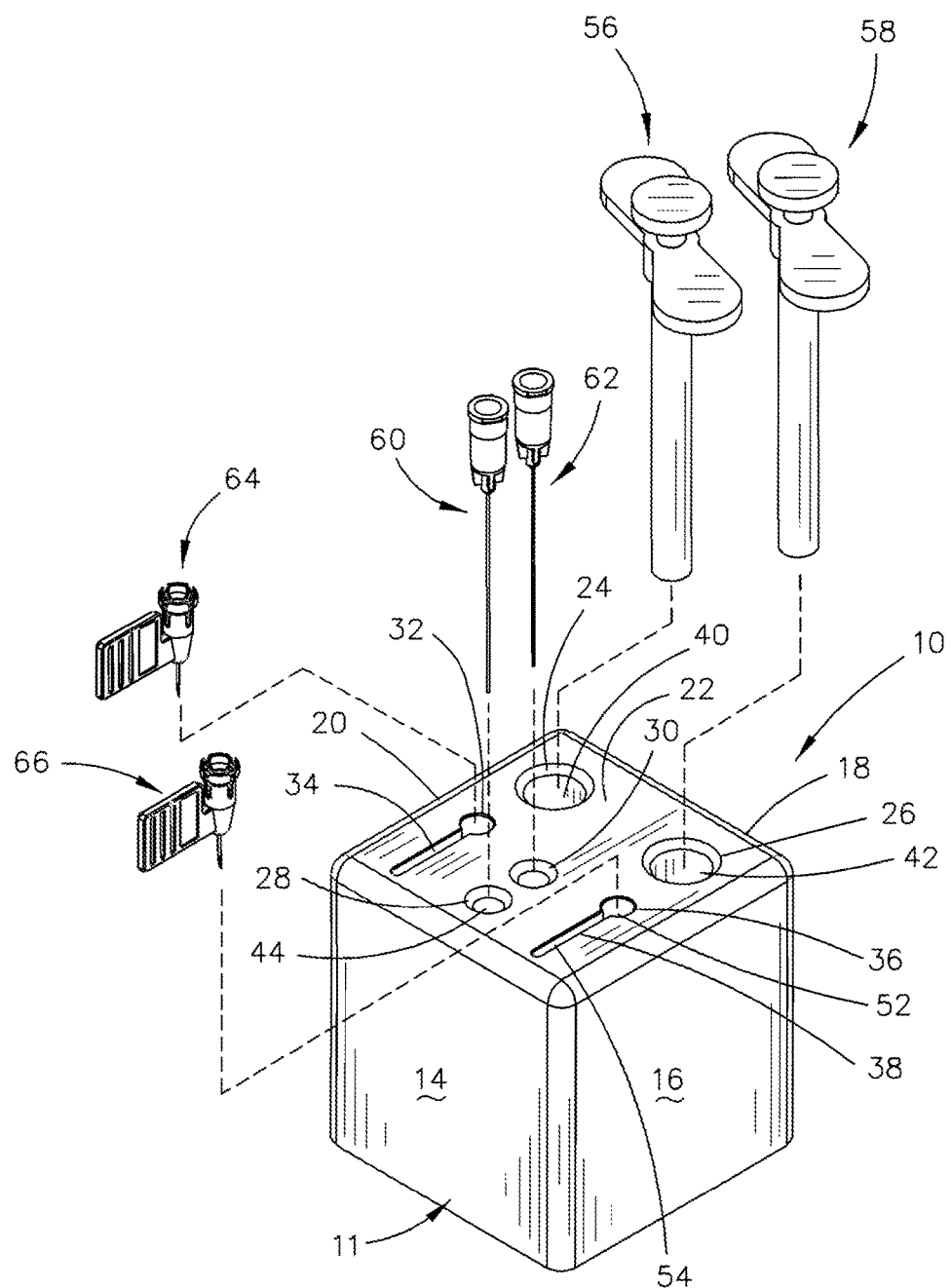
FIG. 2 is an exploded perspective view of the embodiment of FIG. 1.
Figure 3:
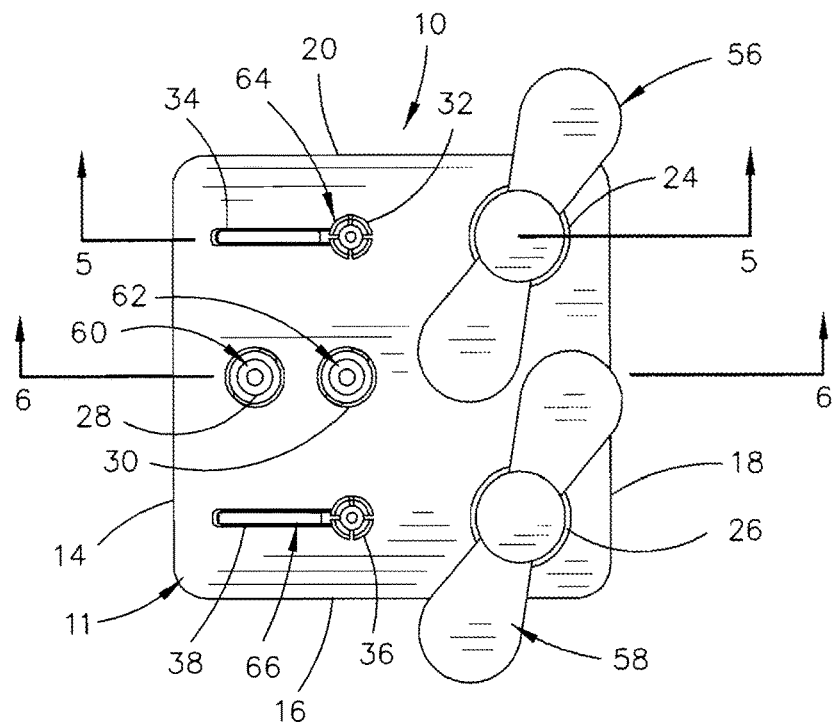
FIG. 3 is a top view of the stand of this invention.
Figure 4:
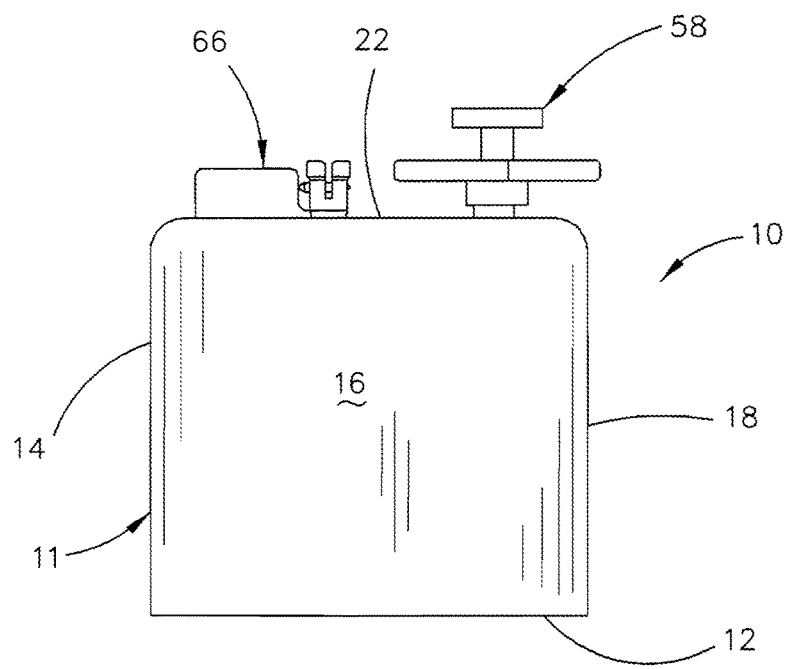
FIG. 4 is a side view of the stand of this invention.
Figure 5:
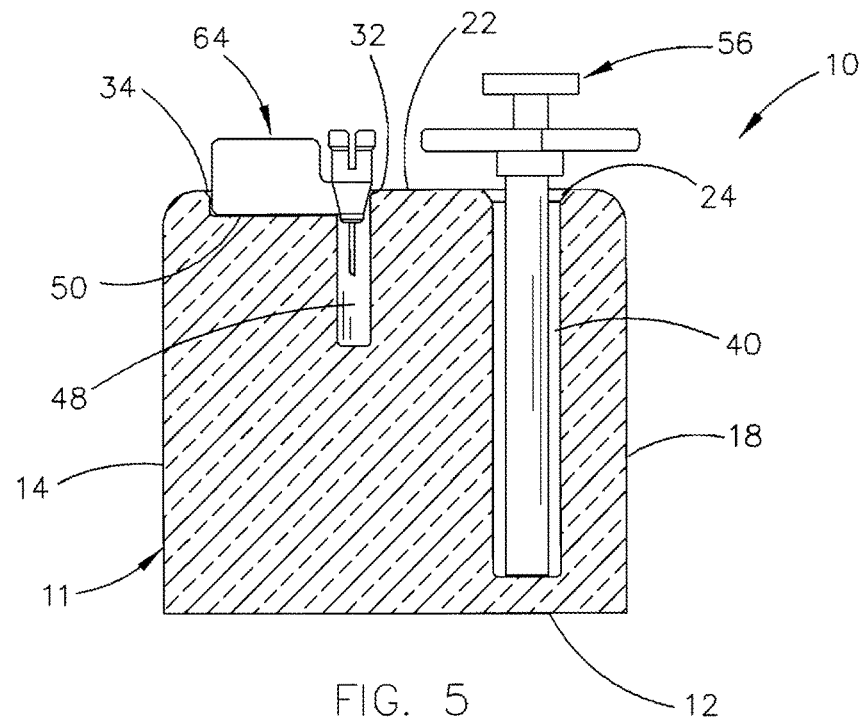
FIG. 5 is a sectional view as seen along lines 5-5 of FIG. 3.
Figure 6:
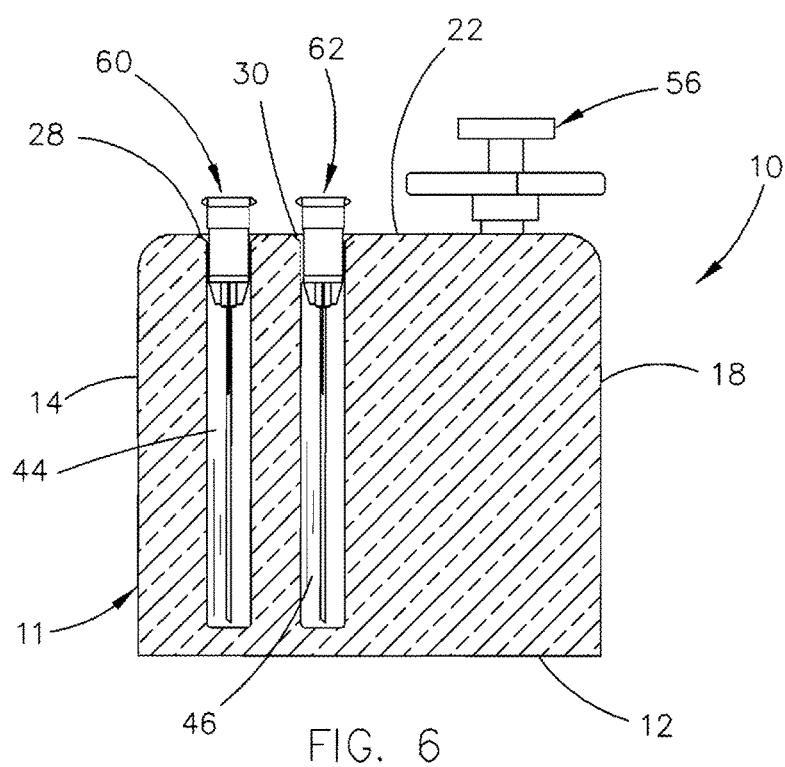
FIG. 6 is a sectional view as seen along lines 6-6 of FIG. 3.

Embodiments are described more fully below with reference to the accompanying figures, which form a part hereof and show, by way of illustration, specific exemplary embodiments. These embodiments are disclosed in sufficient detail to enable those skilled in the art to practice the invention. However, embodiments may be implemented in many different forms and should not be construed as being limited to the embodiments set forth herein. The following detailed description is, therefore, not to be taken in a limiting sense in that the scope of the present invention is defined only by the appended claims.

The numeral 10 refers to the sterile support of this invention which includes a housing 11. Although the support 10 is preferably square-shaped as seen in the drawings, support 10 could have a rectangular shape, a cylindrical shape, or some other shape as will be pointed out hereinafter. Support 10 is of solid block configuration and is comprised of a suitable plastic material. Housing 11 includes a horizontally disposed lower end 12 and vertically disposed sides 14, 16, 18 and 20. Housing 11 also includes an upper end 22 which extends between the upper ends of sides 14, 16, 18 and 20.

Upper end 22 has a pair of spaced-apart chamfered openings 24 and 26 formed therein. Upper end 22 also has a pair of spaced-apart chamfered openings 28 and 30 formed therein. Upper end 22 also has a chamfered opening 32 formed therein. An elongated and horizontally disposed slot 34 is formed in the upper end 22 of housing 11 which extends laterally from opening 32. Upper end 22 also has a chamfered opening 36 formed therein. An elongated and horizontally disposed slot 38 is formed in upper end 22 of housing 11 which extends laterally from opening 36.

The numeral 40 refers to an elongated cylindrical bore in housing 11 which extends downwardly from the chamfered opening 24 towards the bottom 12 of the housing 11 whereby the lower end of bore 40 is closed. The numeral 42 refers to an elongated cylindrical bore formed in housing 11 which extends downwardly from the chamfered opening 26 towards the bottom 12 of the housing 11 whereby the lower end of bore 42 is closed. The numeral 44 refers to an elongated cylindrical bore formed in housing 11 which extends downwardly from the chamfered opening 28 towards the bottom 12 of housing 11 whereby the lower end of bore 44 is closed. The numeral 46 refers to an elongated cylindrical bore formed in housing 11 which extends downwardly from the chamfered opening 30 towards the bottom 12 of housing 11 whereby the lower end of bore 46 is closed.

An elongated cylindrical bore 48 is formed in housing 11 which extends downwardly from opening 32. An elongated slot 50 is formed in housing 11 which extends downwardly from slot 34. An elongated cylindrical bore 52 is formed in housing 11 which extends downwardly from opening 36. An elongated slot 54 is formed in housing 11 which extends downwardly from slot 38.

The numeral 56 refers to a syringe which may be selectively positioned in opening 24 and bore 40. The numeral 58 refers to a syringe which may be selectively positioned in opening 26 and bore 42. The numeral 60 refers to a blunt-tip cannula or epidural needle which may be positioned in opening 28 and bore 44. The numeral 62 refers to a blunt-tip cannula or epidural needle which may be positioned in opening 30 and bore 46. The numeral 64 refers to an injection needle assembly which may be positioned in opening 32, bore 48, slot 34 and slot 50. The numeral 66 refers to an injection needle assembly which may be positioned in opening 36, bore 52, slot 38 and slot 54.

Figure 7:
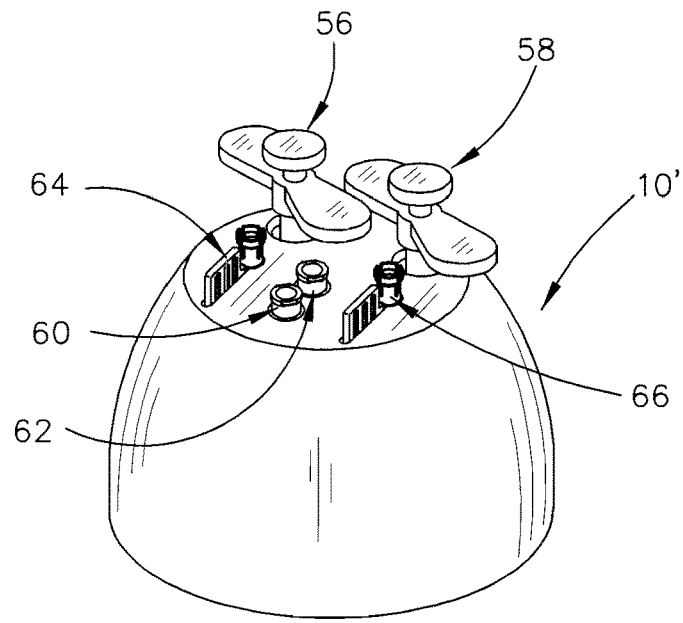
FIG. 7 is a perspective view of a modified form of the stand.
Figure 8:
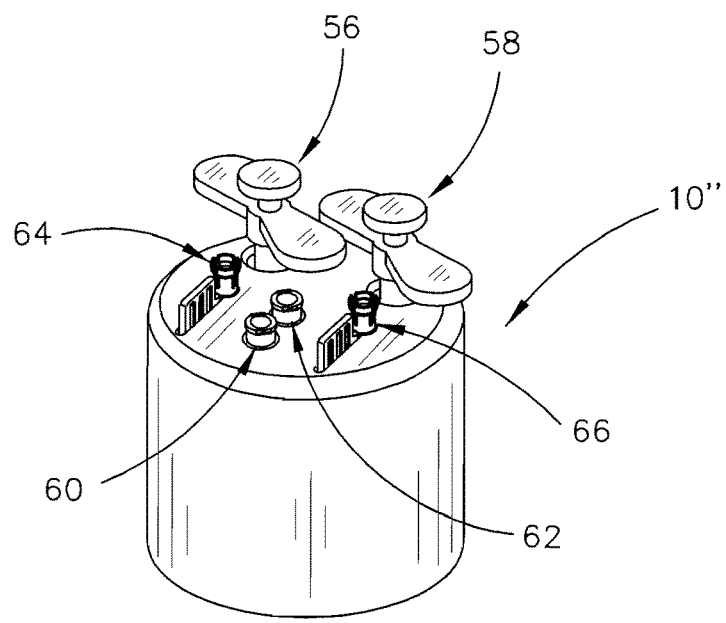
FIG. 8 is a modified version of the stand of this invention.

As stated above, the stand 10 may have other shapes. For example, see FIG. 7 wherein the stand 10' has curved sides. FIG. 8 illustrates another embodiment of the stand 10' wherein the sides of the stand are cylindrical.

Thus it can be seen that an improved stand has been provided for supporting surgical instruments or medical tools therein.

Thus it can be seen that the invention accomplishes at least all of its stated objectives.

Although the invention has been described in language that is specific to certain structures and methodological steps, it is to be understood that the invention defined in the appended claims is not necessarily limited to the specific structures and/or steps described. Rather, the specific aspects and steps are described as forms of implementing the claimed invention. Since many embodiments of the invention can be practiced without departing from the spirit and scope of the invention, the invention resides in the claims hereinafter appended.

We claim:

1. A sterile stand for supporting sterile surgical instruments in a vertically disposed sterile manner, comprising:

a sterile housing including a horizontally disposed upper end and a lower end;

a first opening formed in said upper end of said sterile housing;

a second opening formed in said upper end of said sterile housing;

a third opening formed in said upper end of said sterile housing;

a fourth opening formed in said upper end of said sterile housing;

a fifth opening formed in said upper end of said sterile housing;

a first elongated and horizontally disposed slot formed in said upper end of said sterile housing, which extends laterally from said fifth opening;

a sixth opening formed in said upper end of said sterile housing;

a second elongated and horizontally disposed slot formed in said upper end of said sterile housing which extends laterally from said sixth opening;

an elongated and vertically disposed first cylindrical bore formed in said sterile housing which has upper and lower ends;

said upper end of said first cylindrical bore being in communication with said first opening and extending downwardly therefrom towards said bottom of said sterile housing whereby said lower end of said first cylindrical bore is closed;

an elongated and vertically disposed second cylindrical bore formed in said sterile housing which has upper and lower ends;

said upper end of said second cylindrical bore being in communication with said second opening and extending downwardly therefrom towards said bottom of said sterile housing whereby said lower end of said second cylindrical bore is closed;

said first opening in said upper end of said sterile housing and said first cylindrical bore being configured to have an elongated first sterile syringe, with upper and lower ends, selectively positioned therein;

said second opening in said upper end of said sterile housing and said second cylindrical bore being configured to have an elongated second sterile syringe, with upper and lower ends, selectively positioned therein;

an elongated and vertically disposed third cylindrical bore having upper and lower ends;

said upper end of said third cylindrical bore being in communication with said third opening and extending downwardly therefrom towards said bottom of said sterile housing whereby said lower end of said third cylindrical bore is closed;

said third opening and said third cylindrical bore being configured to have an elongated and sterile blunt-tip cannula or a sterile epidural needle, having upper and lower ends, positioned therein;

an elongated and vertically disposed fourth cylindrical bore having upper and lower ends;

said upper end of said fourth cylindrical bore being in communication with said fourth opening and extending downwardly therefrom towards said bottom of said sterile housing hereby said lower end of said fourth cylindrical bore is closed;

said fourth opening and said fourth cylindrical bore being configured to have an elongated and sterile blunt-tip cannula or a sterile epidural needle, having upper and lower ends, positioned therein;

an elongated fifth cylindrical bore having upper and lower ends;

said upper end of said fifth cylindrical bore being in communication with said fifth opening and extending downwardly therefrom towards said bottom of said sterile housing whereby said lower end of said fifth cylindrical bore is closed;

said upper end of said sterile housing being spaced above said lower end of said sterile housing whereby said upper ends of said first and second elongated and sterile syringes are positioned adjacent said upper end of said sterile housing when said first and second elongated and sterile syringes are positioned in said first opening and said first cylindrical bore and said second opening and said second cylindrical bore respectively;

said upper end of said sterile housing being spaced above said lower end of said sterile housing whereby said upper ends of said elongated and sterile blunt-tip cannulas or sterile epidural needles are positioned adjacent said upper end of said sterile housing when said sterile blunt-tip cannulas or sterile epidural needles are positioned in said third opening and said third bore and said fourth opening and said fourth bore respectively;

said horizontally disposed first slot in said sterile housing having an upper end and a lower end;

said fifth opening, said fifth cylindrical bore and said first slot being configured to have a sterile injection needle assembly, with upper and lower ends, selectively positioned therein;

an elongated sixth cylindrical bore having upper and lower ends;

said upper end of said sixth cylindrical bore being in communication with said sixth opening;

said horizontally disposed second slot in said sterile housing having an upper end and a lower end;

said sixth opening, said sixth cylindrical bore and said second slot being configured to have a sterile injection needle assembly selectively positioned therein;

the upper end of the sterile injection needle assembly being positioned at the upper end of said sterile housing when the sterile injection needle assembly is positioned in said fifth opening, said fifth cylindrical bore and said first slot; and the upper end of the sterile injection needle assembly being positioned at the upper end of said sterile housing when a sterile injection needle assembly is positioned in said sixth opening, said sixth cylindrical bore and said second slot.

* * * * *